United States Patent [19]

Alt

[11] Patent Number: 5,354,317
[45] Date of Patent: Oct. 11, 1994

[54] APPARATUS AND METHOD FOR CARDIAC PACING RESPONSIVE TO PATIENT POSITION

[75] Inventor: Eckhard Alt, Ottobrunn, Fed. Rep. of Germany

[73] Assignee: Intermedics, Inc., Angleton, Tex.

[21] Appl. No.: 863,166

[22] Filed: Apr. 3, 1992

[51] Int. Cl.$^5$ ............................................. A61N 1/365
[52] U.S. Cl. ...................................... 607/19; 128/782
[58] Field of Search ................. 128/419 PG, 421, 782

[56] References Cited

U.S. PATENT DOCUMENTS

| | | | |
|---|---|---|---|
| 4,771,780 | 9/1988 | Sholder | 128/419 PG |
| 4,846,195 | 7/1989 | Alt | 128/782 |
| 4,886,064 | 12/1989 | Strandberg | 128/419 PG |
| 5,014,700 | 5/1991 | Alt | 607/19 |
| 5,031,618 | 7/1991 | Mullett | 128/421 |
| 5,074,302 | 12/1991 | Poore et al. | 128/419 PG |

*Primary Examiner*—William E. Kamm
*Attorney, Agent, or Firm*—O'Connor, Cavanagh

[57] ABSTRACT

An implantable variable rate cardiac pacemaker adaptive to patient exercise has a sensor responsive to each of several preselected different static physical positions of the implant patient to produce electrical output signals uniquely representative of the different physical positions. The pulse generator of the pacemaker is responsive to each output signal of the sensor to generate pacing pulses at a rate different from the rates generated in response to each of the other output signals of the sensor, so that each preselected different physical position has its own representative pacing pulse rate for stimulation of the patient's heart. The generator includes a rate control section adapted to respond to a change by the implant patient from one preselected physical position to another by producing a predetermined pattern of transition from the rate representative of the old position to the rate representative of the new position. In circumstances where the old position is a supine, reclining or prone position and the new position is standing, the rate control is effected to cause a transition from the old rate (for lying or seated reclining position) to the new rate (for the standing position) by first abruptly increasing the rate to a magnitude substantially exceeding the desired new rate and then gradually reducing the magnitude to the new rate. In other position changes, a smooth transition is effected between the old and new rates.

13 Claims, 4 Drawing Sheets

APPARATUS AND METHOD FOR CARDIAC PACING RESPONSIVE TO PATIENT POSITION

BACKGROUND OF THE INVENTION

The present invention relates generally to implantable cardiac pacemakers, and more particularly to a pacemaker which is responsive to a change in the position or posture of the patient to stimulate the patient's heart at a pacing rate which is appropriate to that position.

In recent years a number of intrinsic and extrinsic parameters which undergo change according to states of rest and of physical exercise by the individual have been proposed for use in controlling the rate at which the individual's heart is to be stimulated by an implanted artificial cardiac pacemaker. The intent is that the patient's heart rate should be adapted to the state of true exercise (or rest) of the patient, simulating the intrinsic heart rate of a healthy person with a normal functioning heart who is undergoing the same conditions of exercise or rest.

Most recently, exercise-responsive pacemakers have been advanced and developed which take advantage of simple and inexpensive activity or motion sensors for control of pacing rate. It was suggested several years ago to convert mechanical forces, accelerations and pressures into electrical energy and/or signals for use in biomedical technology. One of the earliest techniques proposed in the patent literature was to generate electrical energy from piezoelectric crystals and other mechanoelectrical converters responsive to movement of the individual to power a device implanted in the individual, as disclosed, for example, in U.S. Pat. Nos. 3,659,615 and 3,456,134. In Journal Biomedizinische Technik 20, pp. 225-228 (1975), Funke described the use of a piezoelectric crystal embedded in silicone rubber and implanted in the pleural space between lung and ribs to detect respiratory rate, for controlling the pacing rate of the patient. U.S. Pat. No. 4,428,380 described using a piezoelectric sensor to measure cardiac activity.

Dahl may have been the first to disclose, in U.S. Pat. No. 4,140,132, the technique of detecting patient activity with a mechanoelectrical converter for the purpose of controlling the rate of a cardiac pacemaker. In Dahl's system, a weighted cantilever arm comprising a piezoelectric crystal is implanted in the patient, the patient's movements cause the cantilever arm to vibrate, the mechanical vibrations are converted to an electrical output signal by the crystal, and the output signal is used as a drive signal for the variable rate pulse generator of the pacemaker. Anderson described a similar system in U.S. Pat. No. 4,428,378 (the "'378 patent"), and used the amplitude of the high frequency content of the converter output signal which was purported to increase with patient movement, as a bandpass signal to control the stimulation rate in an activity-responsive cardiac pacemaker.

Devices such as activity or motion sensors have the distinct advantage that they provide virtually immediate response to patient movements or external forces to generate electrical signals for use in controlling the stimulation pulse rate of the implanted pacemaker. However, they have exhibited serious disadvantages, such as the adverse effect of noise disturbances external to the body, from nearby operating machinery, for example, or emanating from within the body, such as coughing, sneezing, laughing, or the like. Such disturbances are unrelated to physical exercise, but affected the heart rate when early accelerometer-type detectors were utilized for control of the pacemaker stimulation rate. The '378 patent and other prior art sources, such as Proceedings of the European Symposium on Cardiac Pacing, editorial Group, pp. 786 to 790, Madrid, 1985, and Biomedizinische Technik, 4, pp. 79 to 84, 1986, assumed that the maximum acceleration values detected by an activity-controlled cardiac pacemaker in a patient undergoing exercise occur in the range of the resonant frequency of the major body compartments such as the thorax and the abdomen, at approximately 10 Hz (hertz), and that the maximum sensitivity should be in the range above 10 Hz.

In U.S. Pat. No. 4,926,863 (the "'863 patent"), the applicant herein teaches that detection of the accelerometer or activity signal in a frequency range below 10 Hz, and indeed, preferably below approximately 4 Hz is actually highly indicative of true physical exercise by the patient. Moreover, restriction of detection signal frequencies to that range discriminates against and avoids undesirable response to disturbances external and internal to the body. As a result, the effect of disturbances unrelated to exercise can be significantly suppressed during use of a mechanoelectrical converter or like transducer to control the pacing rate.

The '863 patent observes that the amplitude maxima of activity-sensed signals arising from exercise such as walking, climbing stairs, running and bicycling occur with rhythmic motion of the body in the low-frequency range below 10 Hz and principally below 4 Hz. In contrast, sudden spasmodic movements unrelated to true metabolic exercise produce amplitude maxima in the higher-frequency range, well above 4 Hz. Accordingly, the effects of the latter movements, as well as noise disturbances, can be excluded by limiting detection to only the low-frequency content.

By using the frequency band below 10 Hz (preferably below approximately 4 Hz) and by establishing different baseline values as ongoing levels of comparison, the activity pacemaker disclosed in the '863 patent provides fast response and reliable pacing at a variable rate adapted to the level of physical exertion of the patient, closely corresponding to the heart rate of a normal healthy person under the same conditions of physical exertion. Also, by using relative changes rather than absolute values of amplitude of the activity signal to adjust stimulation rate, rate increases are a function of whether a particular baseline value is exceeded and of the actual rate at that time, resulting in smaller rate increases at the higher absolute rates.

In U.S. Pat. No. 5,031,615 (the "'615 patent"), which is a continuation of the '863 patent, the applicant herein discloses an accelerometer and related processing circuitry which are fabricated in hybrid semiconductor integrated circuit form. The accelerometer is designed in that form as a microminiature mechanoelectrical converter or transducer of suitably low power consumption which, as a consequence of its own construction or of use of associated filter circuitry, provides low pass filtering in a frequency band below 10 Hz and preferably below about 4 Hz.

The '863 and '615 patents are incorporated herein in their entirety by reference.

In a copending U.S. patent application Ser. No. 07/863,093, hereinafter referred to as '093 application" of the applicant herein, filed on the same date as the instant application and assigned to the same assignee, an activity pacemaker is programmed to provide different response rates for different types of physical activity of the patient, such as walking, running and bicycling, based on an algorithmic curve which represents the desired and physiologically appropriate heart rates relative to acceleration force. Each type of activity is represented either by a distinct and different portion of the curve of heart rate versus acceleration force with a transition rate between the different portions, or by separate curves which represent distinct and different ones of the activity types. In this way, the patient's heart rate is adapted to different types of activity which, although they may involve the same workload, can have different demands on the patient's cardiovascular system.

These advances and refinements in cardiac pacing have brought about a simple and effective device which is capable of tracking the patient's physical activity constituting true exercise and of controlling the pacing rate of the implanted pacemaker to meet the physiological needs of the patient. To date, however, no device has been suggested which is effective to accommodate the needs of the pacemaker patient's cardiovascular system according to the patient's specific static physical position or posture of the patient (other than a single resting rate), or a change from one such position to another.

It is a principal object of the present invention to provide apparatus and methods for additionally controlling the stimulation rate of an activity pacemaker so that the proper rate is generated in response to the particular static physical position or posture of the patient, such as standing, reclining and lying down, and in response to changes from one position to another.

When a healthy individual with a normal cardiovascular system gets up from a lying or reclining position to a standing position, his or her heart rate increases. If that change of position is followed immediately by some additional activity such as walking, the heart rate may remain at the elevated level or, depending on the level of the activity, increase further. But if the individual simply continues to stand after having arisen, the heart rate more gradually decreases to the resting rate. And if the individual then returns to and remains in a lying position, the heart rate will further decrease to the resting rate characteristic of that position.

It is therefore another important object of the present invention to provide an implantable activity-type pacemaker which detects different physical positions of the patient and responds by generating a pacing rate which is physiologically appropriate for the specific position, each position having its own associated stimulation rate, and by effecting a transition in rates which is appropriate for the change from one position to another whether or not further activity ensues.

SUMMARY OF THE INVENTION

According to the invention, the accelerometer or other motion sensor of the activity pacemaker is configured and calibrated to produce a static output which depends upon the static physical position or posture of the patient in which the device is implanted. If, for example, the sensor is oriented vertically when implanted (and therefore detects movement of the patient preferentially in a horizontal axis), and in that position produces a zero g (i.e., unit of gravity) output, and in one aspect of horizontal orientation of the sensor (i.e., one major side down) produces a $+1$ g output, and in the opposite aspect of horizontal orientation (the other major side down) produces a $-1$ g output, the device will operate as a position sensor.

The position sensor may now be used for two different functions. One function is to establish a base rate for each of two or more different orientations of the sensor, and, thereby, for different positions of the patient in whom it is implanted corresponding to those sensor orientations. For example, the base rate may be 70 beats per minute (bpm) for the standing or upright position (to track a zero g output of the sensor with a vertical orientation), 60 bpm for the supine or reclining position (for a $+1$ g output of the sensor with a horizontal orientation in one aspect), and 65 bpm for the prostrate or prone position (for a $-1$ g output of the sensor with a horizontal orientation in the opposite aspect). The particular base rate is selected according to the normal average rate for a healthy individual in that position, and the suitability to the particular patient. These positional base rates are modified by calibration for slight deviations of the orientation of the sensor, and corresponding deviations of the output, when the implant patient is in those three positions. That is, the thorax typically is somewhat inclined when the individual is standing up or lying down, because the individual is not completely vertical or horizontal in those two positions.

In addition to the advantage that the pacing rate is appropriate to each of several stable positions of the patient, a significant power saving is achieved by reducing the pacing rate to a lower rate in a supine position at night and because no clock is required to establish these stable or static rates. The rate can be properly adjusted merely by analyzing the sensor output.

One function of the activity sensor of the invention, then, is to detect the patient's position and adjust the rate accordingly. The second function of the sensor in its role as a position sensor according to the invention is to initiate a change in rate for a change in the patient's position. The most significant change would be from the supine position, or from the prone position, to the upright position. When that occurs, an elevated rate is triggered to, say, 85 bpm for a brief period to compensate for the physiologic drop in cardiac stroke volume of the patient in changing positions, followed by a gradual decrease in the pacing rate to the base rate for the new position, here 70 bpm. This "overshoot" in rate simulates the normal response of the heart in a healthy individual. Some hysteresis may be used for modification of the rate in other instances of change of position, e.g., from a standing position to a supine position, or from lying on the back to lying on the stomach, by integration to produce gradual changes.

Hence, it is a further object of the invention to provide an implantable cardiac pacemaker which is adapted to sense and respond to a change from a lying or sitting position of the patient to a standing position, by triggering an abrupt and brief increase in the patient's heart rate followed by a gradual fallback to a standing position base rate, and which is adapted to sense and respond to other changes in position of the patient to produce a gradual change of rate.

The capability of the activity sensor to act as a position sensor, and the further provision of rate control in the implanted pacemaker to generate a responsive rate suited to the stable or static position of the patient, does not affect the capability of the activity pacemaker to respond to dynamic changes which arise from true physical exercise by the patient. However, the position sensing and rate control aspect may be used in exercise pacemakers which employ other physiologic parameters for detecting patient exercise, rather than the type which employs an activity sensor for that purpose.

According to an important aspect of the invention, apparatus for controlling the rate of a variable rate implantable cardiac pacemaker responsive to a control signal derived from an accelerometer worn by a patient provides improvements in producing a first signal having a variable value indicative of the extent and continuity of physical exercise by the patient, a second signal having a set of discrete values indicative of different physical positions of the patient during rest, and a third signal having values abruptly varying between different ones of the discrete values indicative of an instantaneous change by the patient from one physical position to another. These improvements reside in part in combining each signal producing means within a single electromechanical converting element making up at least a portion of the accelerometer for sensing physical exercise, physical positions and change in physical positions of the patient. The signal produced by each of these means is part of the control signal.

In the preferred embodiment, the single electromechanical converting element is integrated in silicon material in an electronic circuit. Rate response control algorithms are established of desired heart rate relative to the instantaneous value of the control signal for exercise, static physical positions and physical position change, for varying the rate of the pacemaker based on the control signal. The rate response control algorithm for physical position change has an overshoot of pacing rate maintained for a predetermined period of time to compensate for a relative decrease in stroke volume for change of physical positions by the patient from supine to upright.

BRIEF DESCRIPTION OF THE DRAWINGS

The above and other objects, aspects, features and attendant advantages of the present invention will become apparent from a consideration of the following detailed description of a presently preferred embodiment and method thereof, taken in conjunction with the accompanying drawings, in which.

DESCRIPTION OF THE PREFERRED EMBODIMENT AND METHOD

Figure 1:
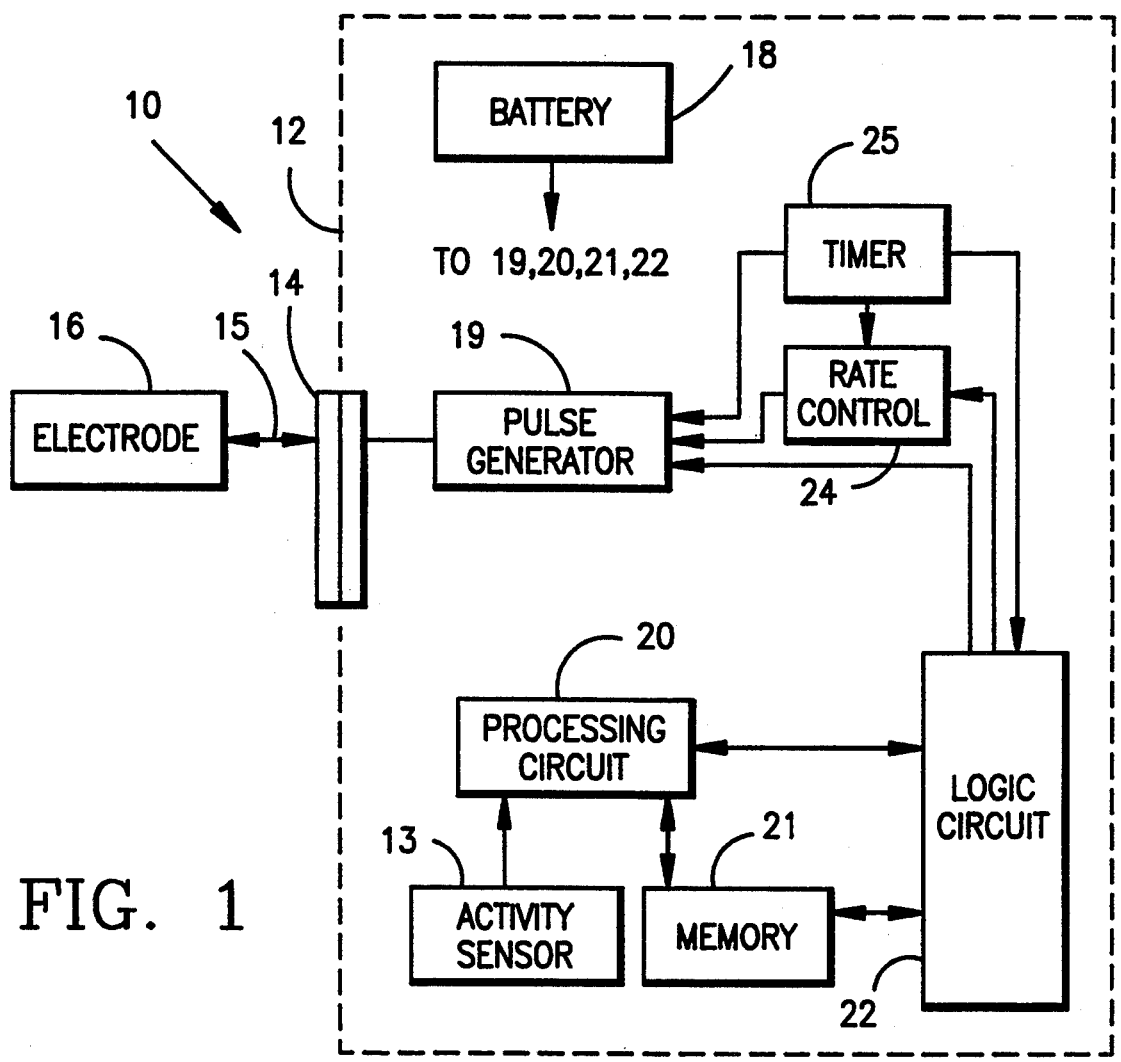
FIG. 1 is a simplified block diagram of an activity rate responsive cardiac pacemaker according to the invention.

Referring to FIG. 1, a programmable cardiac pacemaker 10 includes a hermetically sealed case 12 composed of biocompatible material, in which the components associated with the pulse generator are housed. The implanted unitary medical device (other than the lead and associated electrode(s)) is commonly referred to as the "pulse generator", although present-day units typically include considerably more than a generator for producing stimulating pulses. In the exemplary embodiment depicted in FIG. 1, the overall pulse generator includes a battery 18, a generator 19 having a controllably variable pulse rate for generating the stimulating pulses to be delivered to the patient's heart, a circuit 20 for processing the output signal from a sensor 13, a programmable nonvolatile semiconductor memory 21 for storing the algorithmic curves and other data for programming the functions of the pacemaker, together with logic circuitry 22 for use in performing the logic functions involved in controlling the operation of a rate control circuit 24 for pulse generator 19. A crystal controlled timer 25 is utilized to control the timing of the logic, rate control and pulse generator.

Figure 7:
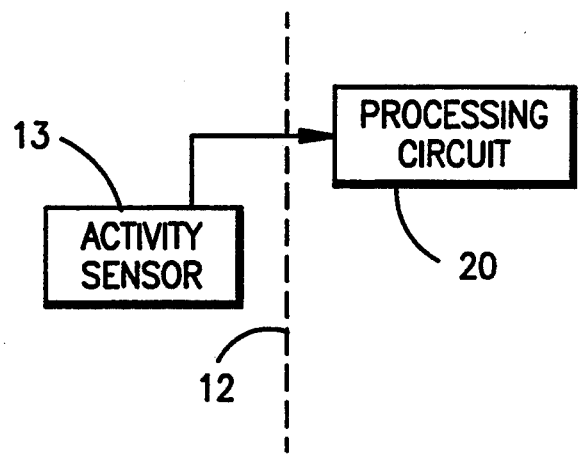
FIG. 7 is a block diagram of an alternative arrangement for the activity (position) sensor relative to the sensor location illustrated in the embodiment of FIG. 1.

The activity sensor 13 is preferably housed within but mechanically isolated from case 12, to avoid being affected by direct pressure on the case. Alternatively, the sensor may be housed in a separate hermetically sealed biocompatible case (also in mechanical isolation therefrom) for implantation separate from unit 10, and electrically connected to the control circuitry thereof by a separate lead, as shown in FIG. 7, where like components are designated by like reference numbers. In the preferred embodiment, sensor 13 comprises an accelerometer of the piezoelectric, piezocapacitive or piezoresistive type, fabricated in hybrid semiconductor integrated circuit form as described in the '615 patent. The sensor may be constructed to exhibit an inherent low pass frequency response characteristic to pass signals in the frequency band below 10 Hz, and preferably below about 4 Hz. Alternatively, the output circuit of the sensor may be connected to a low pass filter in processing circuit 20. Such filtering significantly improves discrimination of the signal components representative of true physical exercise by the patient and other signal components which are unrelated to physical exercise, as detailed in the '615 patent and the '863 patent.

The output circuit of generator 19 is coupled to an electrical connector 14 in the form of a conventional header on the device case 12, which accepts the proximal end of a pacing lead 15 having a stimulating electrode or electrode array 16 at its distal end. Pacing lead 15 is typically of the endocardial type for insertion of the stimulating electrode through the superior vena cava and into the preselected chamber(s) of the right side of the patient's heart for excitation (and sensing of electrical activity) of the myocardial tissue. The pacemaker may be configured for unipolar or bipolar stimulation.

Figure 2:
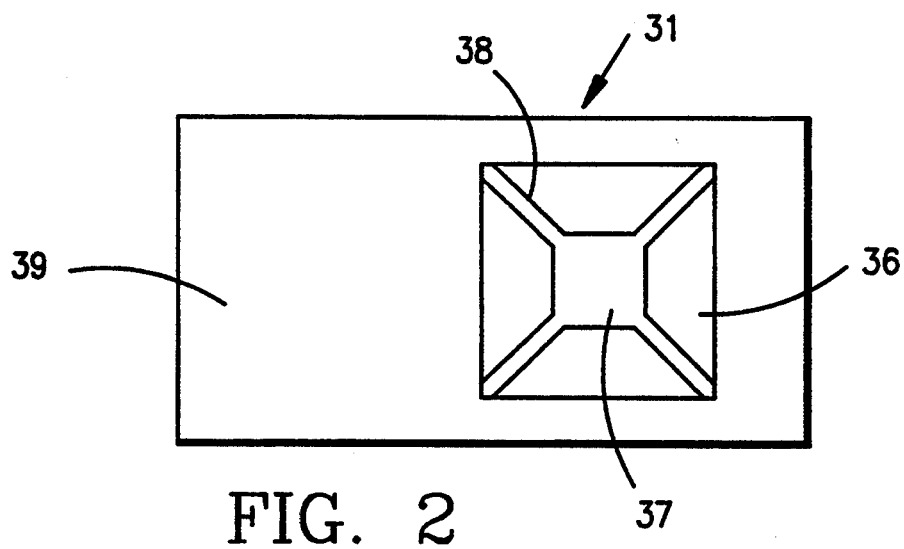
FIG. 2 is a simplified top view of a portion of a hybrid semiconductor device of the type described in the '615 patent including a transducer which may be used as an activity sensor or accelerometer in or in conjunction with the pulse generator portion of the pacemaker of FIG. 1, in the preferred embodiment of the present invention.

FIG. 2 is a top view of an exemplary embodiment of a mechanoelectrical transducer which may be used as the activity/position sensor in a pacemaker according to the invention, but this is an illustrative example only and not intended to be limiting. The reader is referred to the '615 patent for additional details of the transducer. For present purposes, it is sufficient to note that the transducer may be a piezoelectric, piezoresistive or piezocapacitive sensor of semiconductor type, and integrated in a hybrid circuit on a silicon chip by use of conventional semiconductor process technology. As a consequence of its construction, the sensor constitutes a miniaturized accelerometer integrated within a semiconductor device.

In its preferred form, sensor 31 is integrated in a hybrid circuit with a signal filter circuit to provide the desired frequency pass band. Alternatively, however, the transducer itself may be fabricated in geometrical configuration to provide the desired low pass frequency characteristic. The structure is formed on a single crystal silicon substrate having a major surface with an overlying highly doped epitaxial layer of the same conductivity type. The principal sensing element, in this example a rectangular plate 37 with four arms 38 formed within a polycrystalline silicon layer between passivating layers of silicon dioxide atop the epitaxial layer, is adapted to produce an electrical output (in millivolts, calibrated in units of accelerational force, or g's) from the circuit in which it is integrated, when it vibrates in response to movement by the patient in which the device is implanted. The suspended plate structure is fabricated by anisotropic etching of the substrate and epitaxial layer to form a well or cavity 36 beneath a portion of the polycrystalline layer, followed by removal of portions of the passivating and polycrystalline layers to leave plate 37 connected by the four arms 38 to the corners of the well. An additional layer 39 deposited on the structure with an opening contiguous with the perimeter of well 36 allows the plate to undergo movement on its arms, and a protective layer such as a glass plate is deposited on the structure.

Figures 3, 4:
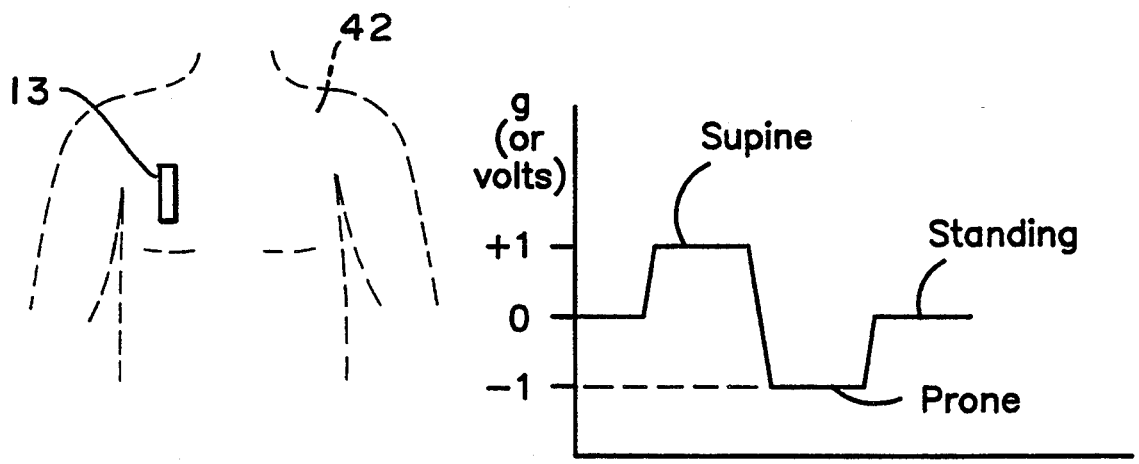
FIG. 3 is a partial front view of a patient showing the orientation of the implanted accelerometer.
FIG. 4 is a chart showing the sensor output for various physical positions of the patient.
Figure 8:
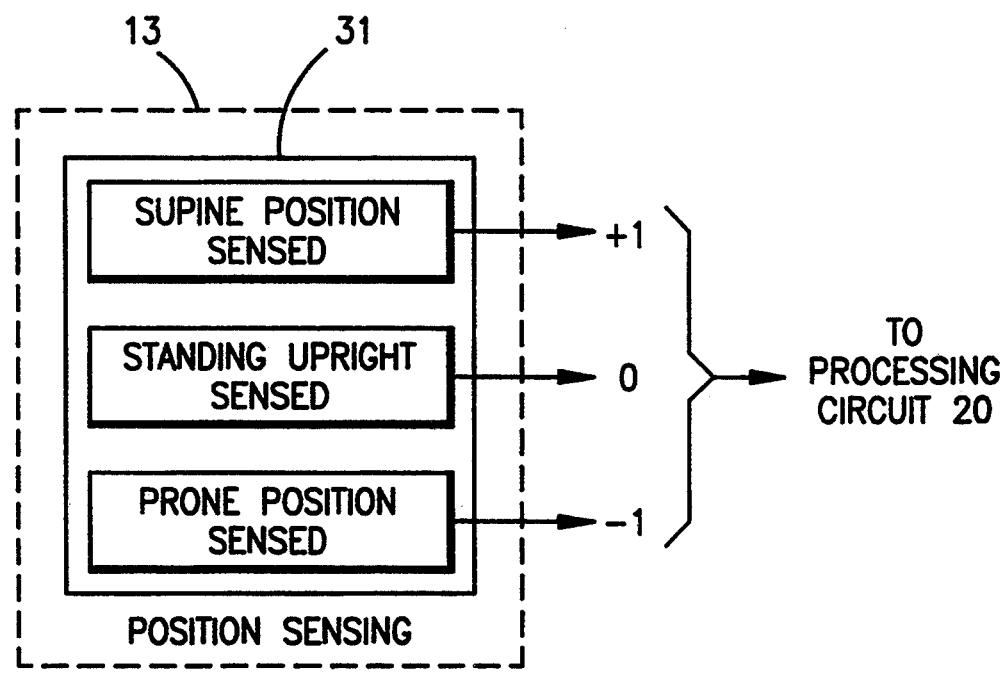
FIG. 8 is a functional block diagram of the activity (position) sensor operation for position sensing.

The suspended plate structure is responsive to earth gravity and to acceleration, and an integrated circuit fabricated in the semiconductor/hybrid structure by known techniques serves to process the signal generated by movement of the plate on its arms. By calibrating the electrical output of this circuit, the orientation of the sensor itself may be determined at least to an extent suitable for purposes of the present invention, so that it may be utilized as a position sensor for detecting the static or stable (i.e., non-moving) position of the patient, as well as an activity sensor responsive to the dynamic movements of the patient. In the preferred embodiment, the calibration produces a static output of $+1$ g arising from the stress on the plate/arms structure when the patient is lying on his back (i.e., in the supine position), and a static output of $-1$ g when the patient is lying on his stomach (i.e., in the prone position), for a vertical orientation of the implanted sensor 13 when the patient 42 is standing (i.e., in the upright position), where a 0 g static output is established, as shown in FIGS. 3 and 4 and in functional form in FIG. 8.

The sensor output signal is processed to provide a separate pacing rate (heart rate) which is unique to each respective identified static position of the patient. By way of example, a rate of 60 bpm may be selected for the supine position, a rate of 65 bpm for the prone position, and a rate of 70 bpm for the standing position. The desire here is to establish this aspect of the rate control of the pulse generator according to static physical position of the patient, in a manner and at a value, level or magnitude which most closely approximates the actual heart rate of a healthy person with a normal cardiovascular system who has assumed that position, and, further, at a rate which is appropriate for the patient in question.

Sensor 13 is used, in the pacemaker according to the present invention, as a position sensor which performs two different functions. The first of these two functions is the establishment of a distinct and different base rate for each distinct and different static physical position of the patient, to the extent that it is desirable to do so and within the distinguishing capabilities of the device. Since it is well established that a healthy subject does experience different heart rates for different static positions, most notably the standing, supine or reclining, and prone positions, it is sufficient to limit the sensing and rate response to the latter positions. The output of the sensor, of course, depends upon its actual orientation relative to the vertical or horizontal. If the sensor is implanted, whether in the pulse generator case or its own case, with a vertical orientation when the patient is standing and with its major surfaces (opposite sides of the rectangular plate) having the aspects of the front and back of the patient, it may and usually would be inclined slightly from the vertical (or the horizontal) by the incline of the thorax, because the individual is not completely vertical in the upright position (nor completely horizontal in the supine or the prone positions). Thus, the orientation of the sensor for different positions of the patient will produce different outputs (in g's) which may be calibrated to provide unique pacing rates, but, again, the process is quite useful for only two or three commonly assumed static positions of the patient. In any event, the calibration should be done after the sensor is implanted, because of the typical inclination of the sensor orientation relative to the vertical or horizontal planes.

In a more advanced version, the pacemaker may be implemented to perform an autocalibration. This may be established by recognizing the static acceleration force of the upright position of the individual, and the dynamic signal variations associated with physical exercise in (and only in) the upright position, such as by walking or bicycling for example. Such autocalibration is performed by the circuitry in the pacemaker 10, including the processing circuit 20, memory 21 and logic circuit 22 (FIG. 1), in conjunction with the sensor 13 and its orientation when the patient is in the upright position. In this way, the calibration is based on the orientation of the transducer when implanted in the patient, and is performed automatically by the pacemaker.

For performing the base rate function, a simple algorithm or logic function may be performed within pulse generator 10 on the sensor 13 output to establish: (1) if 0 g, rate is 70 bpm; (2) if $-1$ g, rate is 65 bpm; (3) if $+1$ g, rate is 60 bpm. This may be done in circuits 20 and/or 22 which, however, are used principally for processing activity signals, such as those and in the manner described in the aforementioned copending docket 133 application.

Figure 5:
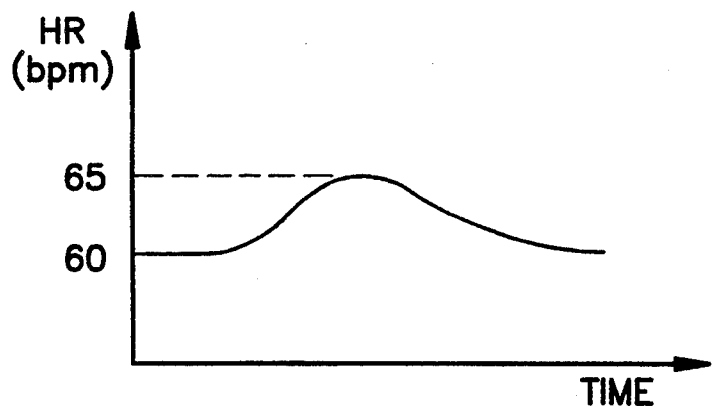
FIG. 5 is a graph illustrating the smoothing or averaging of the pacing rate as it is varied during a change of positions by the patient.
Figure 6:
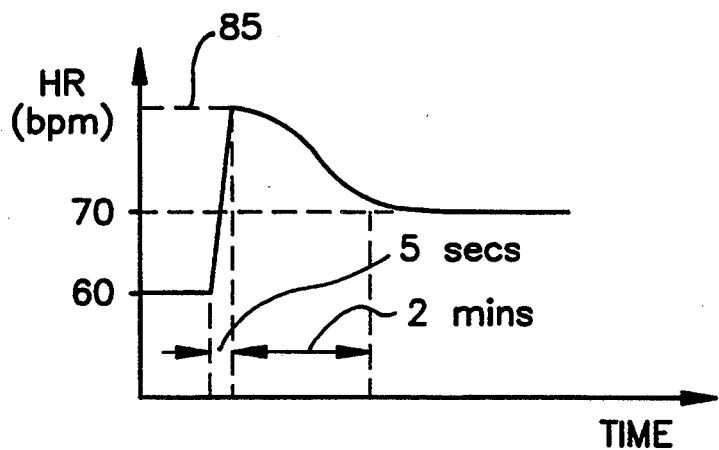
FIG. 6 is a graph illustrating the particular pattern of a variation of the pacing rate for a change from a lying position to a standing position by the patient.

The second function of the sensor in the pacemaker of the present invention is to detect and respond or produce a response to a change by the patient from one static physical position to another, which will be described with reference to FIGS. 5 and 6. In the process of changing from one static position to another, of course, there is movement which is detected as patient activity by the sensor. It is important to understand, however, that even in the absence of activity, the pulse generator is essentially programmed to deliver a pacing rate based on the particular physical position of the patient, assuming that a specific rate has been established for that position, or, if not, a predetermined resting rate. If the patient is in the supine position, the rate, in this example, is 60 bpm. If the patient then moves in slow deliberate fashion to a prone position, the processing circuit 20 performs an integration or averaging function to smooth the transition from 60 bpm to the 65 bpm set for the patient when lying on his stomach. Thus, the sensor output is analyzed and hysteresis is used for smoothing or averaging the modification of the rate, as shown in the simplified graph of FIG. 5. If the patient were to lie down from a standing position into the supine position, the rate is adjusted gradually from 70 to 60 bpm by the processing circuitry in conjunction with the rate control circuitry of the pulse generator.

Assume further, that the patient changes from the supine position (or from the prone position) to the upright position. For that event, the overall circuit which governs rate control is programmed to produce a spike response to abruptly elevate the heart rate to, say, 85 bpm to compensate for the physiologic drop in cardiac stroke volume of the patient in standing up, and to then gradually decrease the rate to 70 bpm which is the established base rate for the standing position. This is illustrated in the simplified graph of FIG. 6. The overshoot in rate corresponds to the normal response of the heart of a healthy individual undergoing the same movement. Operation of the pacemaker in this respect is performed according to a decision rule by which recognition is made of the sensor output signal as this change of position from supine to upright is made by the patient, and which distinguishes this output signal from other forms of activity.

In the preferred embodiment, the abrupt increase from 60 to 85 bpm in these circumstances is accomplished in five seconds, while the gradual decrease to 70 bpm thereafter takes about two minutes. This algorithm prevents the patient's blood pressure from dropping when he stands up (a similar algorithm may be used for a change in position from a reclining seated position to a standing position), and provides a physiological fallback to the proper rate absent other activity by the patient.

Figure 9:
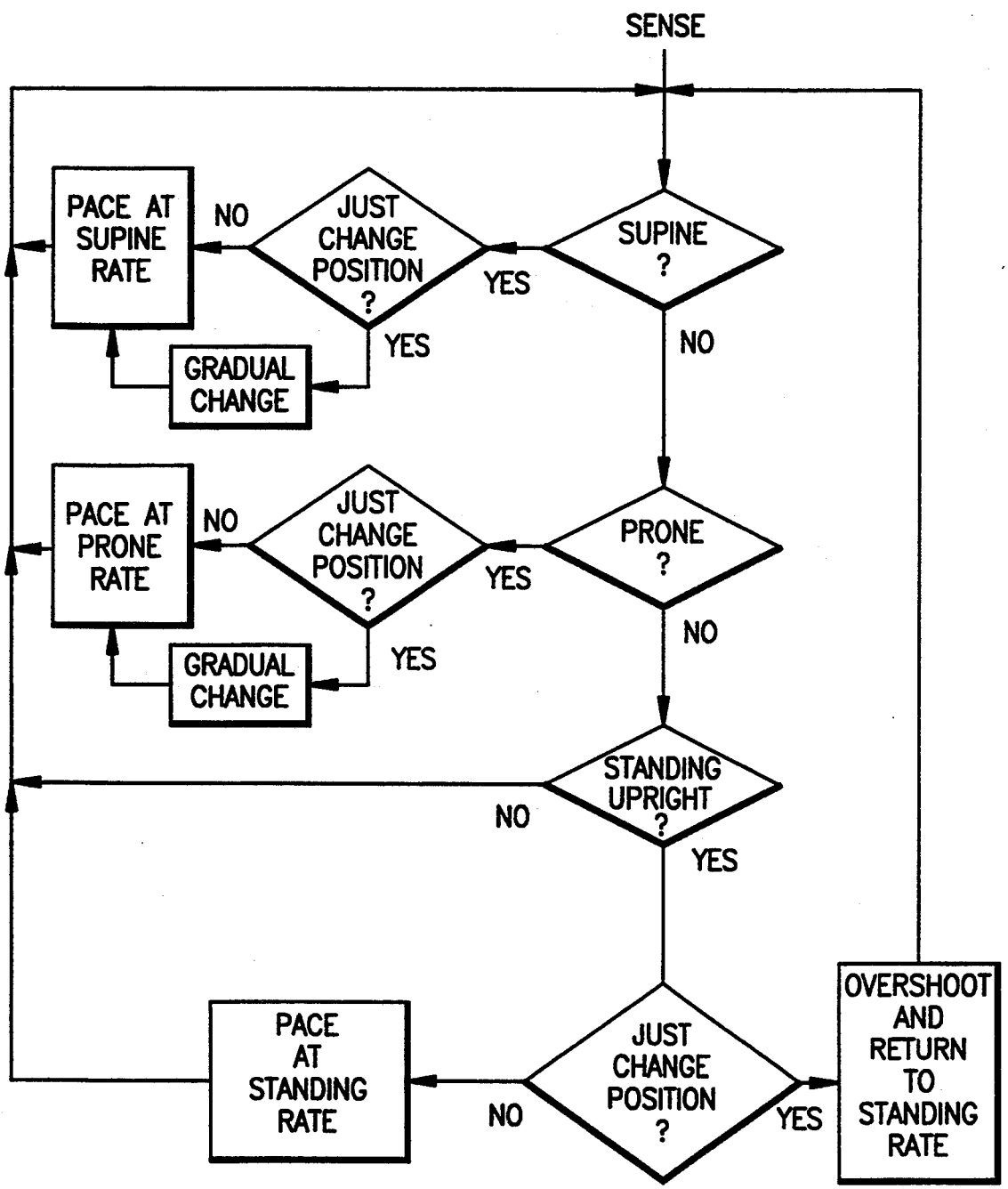
FIG. 9 is a flow diagram useful for describing the operation of the device in response to a sense signal from the activity (position) sensor.

The overall operating method or algorithm of the device is illustrated in the flow diagram of FIG. 9. The pacing rate for the patient's physical position is determined from the sense signal output of the position sensor, and the transition from one position-based rate to another also takes account of recent status including any change in the patient's position.

It will be appreciated from the foregoing description of the invention and its various aspects and features, that implantable medical devices for exercising selective cardiac control are provided which are capable of sensing the position and change of position of the patient and of responding with a pacing rate or varying (transitioning) rate which is appropriate for that position or change. It is worth emphasizing that an accelerometer having a different design from that described herein may be used, more than a single activity sensor may be used, and that the same or other activity sensors may be used to detect exercise by the patient and to produce an appropriate response thereto. Additionally, the position sensor of the present invention may be used in so-called rate-responsive or rate-adaptive pacemakers which do not rely on activity sensing but rather on other, intrinsic physiologic parameters (such as blood temperature, oxygen saturation, respiration, minute ventilation, etc.) to detect patient exercise.

It is significant that a single electromechanical converting element of the accelerometer senses each of physical exercise, physical position and change in physical positions of the patient. The signal produced by the combined elements is part of the control signal used for controlling the rate of the implantable pacemaker.

Thus, although a preferred embodiment and method have been disclosed herein, it will be apparent to those skilled in the art from a consideration of the foregoing description that variations and modifications may be made without departing from the true spirit and scope of the invention. Accordingly, it is intended that the invention shall be limited only to the extent required by the appended claims and the rules and principles of applicable law.

What is claimed is:

1. A cardiac pacing device adapted to be implanted in a patient and to have a variable pacing rate adaptive to patient exercise, comprising:

sensor means adapted to respond to a plurality of preselected distinct and different static physical positions of the patient for producing electrical output signals uniquely representative of the distinct and different physical positions, pulse generator means responsive to each said uniquely representative electrical output signal produced by said sensor means for generating pacing pulses at a rate which is different from the rates generated in response to each of the other uniquely representative electrical output signals produced by said sensor means, so that each preselected distinct and different physical position among said plurality of preselected distinct and different static physical positions of the patient has its own representative pacing pulse rate, to stimulate the patient's heart, said pulse generator means including transitioning means responsive to a change from a static physical position of lying to a static physical position of standing for abruptly increasing the rate to a value exceeding the rate representative of standing and for thereafter gradually reducing the rate to the rate representative of standing.

2. The cardiac pacing device of claim 1 wherein: said sensor means comprises an accelerometer.

3. The cardiac pacing device of claim 2, further including:

a case in which said pulse generator means is housed, and means for mechanically isolating the accelerometer from the case to render it unresponsive to pressure on the case.

4. The cardiac pacing device of claim 2, further including:

a case in which said pulse generator means is housed, and a second case in which said accelerometer is housed in mechanical isolation for implantation in the patient separately from the case for said pulse generator means.

5. The cardiac pacing device of claim 2, wherein:

said accelerometer comprises a hybrid semiconductor structure.

6. The cardiac pacing device of claim 5, wherein: said accelerometer comprises a composition selected from the group consisting of piezoelectric, piezocapacitive and piezoresistive material.

7. The cardiac pacing device of claim 2, wherein: said sensor means includes a silicon integrated circuit containing said accelerometer.

8. The cardiac pacing device of claim 1, wherein: said transitioning means includes hysteresis means responsive to a change in the patient's physical position from standing to another static physical position for smoothly varying the rate from the rate representative of standing to the rate representative of said another static physical position.

9. A method of providing an implantable cardiac pacemaker sensitive to certain preselected relatively static physical positions of the patient in whom the pacemaker is implanted, which comprises:

providing a mechanoelectrical transducer which produces a plurality of distinct and different electrical outputs in response to and respectively uniquely representative of a plurality of distinct and different static orientations of the transducer relative to a horizontal plane, providing a programmable pulse generator for implantation with and electrical connection to the transducer so that each of the distinct and different electrical outputs of the transducer representative of distinct and different static orientations of the transducer causes the pulse generator to generate pacing pulses at different rates uniquely corresponding to the different electrical outputs of the transducer and, thereby, to the different orientations of the transducer, calibrating the different rates for the different electrical outputs to correspond to a desired heart rate for each preselected static physical position of the implant patient, based on the orientation of the transducer when implanted in the patient, so that the rate at which pacing pulses are generated depends at least in part on the patient's static physical position and a change in pacing pulse rate occurs when the patient changes from one physical position to another dictating a different rate, and implementing the pacemaker to perform an algorithm to recognize the electrical output produced by the transducer when the patient changes position from supine to upright as distinguished from other forms of activity of the patient, and to respond when such recognition occurs to abruptly increase the rate to a level above the normal rate for the upright position with a gradual return to said normal rate, to compensate for the physiologic drop in cardiac stroke volume of the patient in such change of positions.

10. The method of claim 9, including implementing the pacemaker for automatically performing the step of calibrating.

11. A method of controlling the pacing rate of an implantable cardiac pacemaker based in part on a plurality of preselected relatively static physical positions of a patient in which the pacemaker is implanted, comprising the pacemaker-implemented steps of:

sensing each of a plurality of preselected distinct and different static physical positions of the patient, developing a plurality of distinct and different electrical signals having a one-to-one correspondence to the sensed plurality of preselected distinct and different static physical positions of the patient, separately employing each of said plurality of distinct and different electrical signals as a pacing rate control signal for the pacemaker according to the sensed static physical positions of the patient at different points in time, and automatically calibrating the pacemaker to generate different pacing rates for each of said different electrical signals employed as a pacing rate control signal to provide a desired heart rate for each preselected static physical position of the patient as the patient assumes each of the preselected static physical positions.

12. The method of claim 11, further including:

sensing a change in physical position of the patient from a supine position to an upright position, and abruptly increasing the pacing rate to a level above a predetermined normal pacing rate for the upright position and gradually returning to said normal rate, to compensate for the physiologic drop in cardiac stroke volume of the patient in said change in physical position from the supine position to the upright position.

13. The method of claim 1, further including:

sensing a change in physical position of the patient from one to another of said preselected static physical positions, and smoothly transitioning the pacing rate of the pacemaker from the rate calibrated for said one position to the rate calibrated for said another position.

* * * * *